(12) United States Patent
Pandiaraj et al.

(10) Patent No.: US 12,279,780 B2
(45) Date of Patent: Apr. 22, 2025

(54) ASSEMBLIES AND KITS FOR REAMING ORTHOPEDIC JOINTS, AND METHOD OF ASSEMBLING REAMER FOR SAID

(71) Applicant: DEPUY IRELAND UNLIMITED COMPANY, Ringaskiddy (IE)

(72) Inventors: Bharathiraj Pandiaraj, Ringaskiddy (GB); Dipumon Ayyanchira Mani, Delhi (IN); Vivek Thunoli, Leeds (GB); Duncan Beedall, Leeds (GB); James Naylor, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 264 days.

(21) Appl. No.: 17/779,312

(22) PCT Filed: Dec. 1, 2020

(86) PCT No.: PCT/EP2020/084165
§ 371 (c)(1),
(2) Date: May 24, 2022

(87) PCT Pub. No.: WO2021/110702
PCT Pub. Date: Jun. 10, 2021

(65) Prior Publication Data
US 2022/0409218 A1    Dec. 29, 2022

(30) Foreign Application Priority Data

Dec. 2, 2019    (IN) .............................. 201911049505

(51) Int. Cl.
*A61B 17/16*    (2006.01)
(52) U.S. Cl.
CPC ...... *A61B 17/1659* (2013.01); *A61B 17/1615* (2013.01); *A61B 17/1666* (2013.01)

(58) Field of Classification Search
CPC ............ A61B 17/1615; A61B 17/1659; A61B 17/1666; A61B 17/1684
See application file for complete search history.

(56) References Cited

U.S. PATENT DOCUMENTS

| 5,299,893 | A | 4/1994 | Salyer |
| 9,101,368 | B2 | 8/2015 | Sidebotham |

(Continued)

FOREIGN PATENT DOCUMENTS

WO    2007097749 A1    8/2007

OTHER PUBLICATIONS

PCT/EP2020/084165—International Search Report dated Feb. 5, 2021.

*Primary Examiner* — Samuel S Hanna
(74) *Attorney, Agent, or Firm* — Barnes & Thornburg LLP (57) ABSTRACT

A system for reaming a bone comprising: a base comprising a connector adapted to couple the base to a driver and a support surface; a first reaming member comprising: a first seating surface shaped to seat the first reaming member over the support surface, a first reaming surface adapted to ream a bone to a first diameter, and a first attachment mechanism attaching the first reaming member to the base; a second reaming member comprising: a second seating surface shaped to seat the second reaming member over the support surface, a second reaming surface adapted to ream a bone to a second diameter, and a second attachment mechanism attaching the second reaming member to the base; wherein the second diameter is larger than the first diameter.

8 Claims, 6 Drawing Sheets

(56) References Cited

U.S. PATENT DOCUMENTS

| | | |
|---|---|---|
| 10,143,480 B2 | 12/2018 | Victor |
| 2008/0195106 A1 | 8/2008 | Sidebotham et al. |
| 2015/0366568 A1 | 12/2015 | Victor |
| 2017/0014141 A1 | 1/2017 | Cameron et al. |
| 2017/0035443 A1* | 2/2017 | Sausen ............... A61B 17/1659 |
| 2019/0262008 A1 | 8/2019 | Lualdi |

* cited by examiner

ASSEMBLIES AND KITS FOR REAMING ORTHOPEDIC JOINTS, AND METHOD OF ASSEMBLING REAMER FOR SAID

CROSS-REFERENCE TO RELATED APPLICATIONS

This application is a National Stage Application filed Under 35 U.S.C. § 371 of International Application No. PCT/EP2020/084165 filed Dec. 1, 2020, which claims priority to Indian application Ser. No. 20/191,1049505 filed Dec. 2, 2019, which is hereby incorporated by reference in its entirety.

FIELD OF THE INVENTION

The present invention relates to assemblies for reaming orthopedic joints, kits for reaming orthopedic joints, methods of assembling reamers for reaming orthopedic joints, and methods of preparing reamers for use in surgery of orthopedic joints.

BACKGROUND TO THE INVENTION

Human and animal bodies have various joints, such as ankles, knees, hips, shoulders and elbows. The joints are formed where two or more skeletal bones meet. Many joints permit movement between those two or more bones. Between the joints of a body that permit motion, typically, cartilage is found.

Cartilage provides lubrication for the motion and absorbs some of the forces to which a joint is subjected. The cartilage may wear down over time causing the bones making up a joint to come into contact leading to pain and reduced joint function.

Other causes of joint damage is arthropathy. Arthropathy, such as arthritis, is a disease of the joint that may lead to conditions such as pain, stiffness and swelling.

A hip joint is one of the joints to may experience degradation or disease. The hip joint is a ball and socket arrangement formed where the femoral head of a femur meets the acetabulum of the pelvis. The femoral head, which is the ball part of the joint, and the acetabulum, which is the socket part of the joint, are coated with cartilage for allowing the femur to articulate relative to the pelvis. Other joints commonly afflicted include those of the spine, knee, shoulder, elbow, carpals, metacarpals, and phalanges of the hand.

An option to treat damaged joints is to replace the parts of the joint that are degraded or diseased with a prosthesis. A commonly used prosthesis is a total joint prosthesis. The total joint prosthesis is used to replace native or natural joint parts with an artificial joint. For example, in a total hip replacement procedure, a natural hip joint may be treated with a total hip replacement prosthesis. The total hip replacement prosthesis includes an artificial femoral part and an artificial acetabular part.

During a surgical procedure to replace a joint, the joint is prepared to receive its respective part using specialized instrumentation. One such instrument is a reamer. Reamers are an instrument used to remove parts of a bone to be replaced and may be used to shape the bone to receive the appropriate prosthetic component.

In a total hip replacement, a reamer may be used to prepare the acetabulum of a recipient to receive a replacement cup prosthesis. Acetabular reamers are typically hemispherical and are used prepare a correspondingly shaped cavity in the acetabulum.

To prepare the cavity, the reamer may be connected to a power tool, which is used to rotate the reamer. The rotating reamer is engaged with the acetabulum and a hemispherical cavity is prepared. The diameter of the reamed cavity is determined by the size of the replacement cup prosthesis that is to be implanted.

For a hip replacement procedure, the diameter of the reamed cavity of the acetabulum may be planned. To reach the planned diameter the physician may start preparing the acetabulum using a reamer with a diameter smaller than planned. The physician may build up to the planned diameter incrementally using reamers with increasing diameters. In a typical procedure, the smaller diameter reamer would be removed and replaced by a larger diameter reamer. The physician then engages the larger diameter reamer with the acetabulum to ream the cavity to the larger diameter.

Known reamers include those disclosed in various patents and patent applications. For example, PCT publication number WO2007/097749 A1 discloses a disposable acetabular reamer and method of fabricating the same. The disclosed disposable acetabular reamer has a cutter blade molded into the surface of a support. The cutter blade is formed of a single flat sheet of metallic material having a series of teeth formed thereon which protrude above the surface of the support such that when the acetabular reamer is rotated, the teeth contact the surface of an acetabulum to ream the bone.

Another known reamer is disclosed in U.S. patent application Ser. No. 14/746,386, which published as US publication number US2015/0366568 A1. The disclosed disposable cutter acetabular reamer comprises a support frame having a plurality of radially extending struts to which a cutting shell is removably connected. The frame serves as a universal support structure that provides added mechanical support and stability to which various embodiments of cutting shells may be connected for the removal of bone and tissue.

A further known reamer is disclosed in U.S. patent application Ser. No. 13/741,211 now U.S. Pat. No. 9,101,368. The disclosed reamer has a cutting tool with a cutting surface on a first side of the cutting tool and an attachment member on a second side of the cutting tool. The cutting surface can have cutting edges with characteristics that vary along the cutting tool.

A yet further known reamer is disclosed in U.S. patent application Ser. No. 858,934, now U.S. Pat. No. 5,299,893. The disclosed reamer is a disposable cutter which has a plurality of cutting edges. The cutter has perforations adjoining the cutting edges. The cutter defines an axis of rotation. The cutter is joined to a transparent bowl. The bowl is concentric with the axis of rotation. The bowl has a bottom tool driver opening concentric with the axis of rotation.

SUMMARY OF THE INVENTION

According to a first aspect of the present invention, there is provided an assembly. The assembly includes a base, a first reaming member and a second reaming member. The base has a connector adapted to couple the base to a driver and a support surface. The first reaming member includes a first seating surface shaped to seat the first reaming member over the support surface. The first reaming member includes a first reaming surface adapted to ream a bone to a first diameter. The first reaming member includes a first attachment mechanism attaching the first reaming member to the base. The second reaming member includes a second seating surface shaped to seat the second reaming member over the first reaming surface. The second reaming member includes a second reaming surface adapted to ream a bone to a second diameter. The second reaming member includes a second attachment mechanism attaching the second reaming member to the base. The second diameter is larger than the first diameter.

Preferably, the first and second reaming members may be releasably attachable to the base.

Preferably, the second reaming surface may be separated from the first reaming surface by a predetermined thickness to thereby increase the second diameter relative to the first diameter.

Preferably, the support surface may have an external shape and the first seating surface has an internal shape that matches the external shape. The external shape may be hemispherical and the internal surface has a curvature that conforms to the external shape.

Preferably, the base may have a first recess extending into the support surface. The first reaming member may have a first prong and a second recess. The second reaming member may have a second prong. The first recess may be configured to receive the first prong in order to attach the first reaming member to the base. The second recess may be configured to receive the second prong in order to attached the second reaming member to the base.

Preferably, the second reaming member may be positioned over the first reaming member and attached to the first reaming member by the second attachment mechanism in order to attach the second reaming member to the base. Preferably, the base may comprise a base coupling to which the first and second attachment mechanisms are couplable. Preferably, the first and second attachment mechanisms are independently couplable to the base coupling.

According to a second aspect of the present invention, there is provided a kit have a base, a first reaming member and a second reaming member. The base may have a connector adapted to couple the base to a driver and a support surface. The first reaming member may have a first seating surface, a first reaming surface and a first attachment mechanism. The first seating surface may be shaped to seat the first reaming member over the support surface. The first reaming surface may be adapted to ream a bone to a first diameter. The first attachment mechanism may be configurable to attach the first reaming member to the base. The second reaming member may have a second seating surface, second reaming surface and a second attachment mechanism. The second seating surface may be shaped to seat the second reaming member over the first reaming surface. The second reaming surface may be adapted to ream a bone to a second diameter. The second attachment mechanism may be configurable to attach the second reaming member to the base. The second diameter may be larger than the first diameter.

According to a third aspect of the present invention, there is provided a method of assembling a reamer. The method may include the steps of:
providing a base comprising a connector adapted to couple the base to a driver and an external surface defining a support surface;
providing first reaming member having:
  a first internal surface shaped to seat the first reaming member on the support surface,
  a first external surface adapted to ream a bone, and
  a first attachment mechanism to attach the first reaming member to the base; engaging the first internal surface with the support surface;
attaching the first reaming member to the base with the first attachment mechanism;
providing a second reaming member having:
  a second internal surface shaped to seat the second reaming member on the first external surface,
  a second external surface adapted to ream a bone, and
  a second attachment mechanism to attach the second reaming member to the base;
engaging the second internal surface with the first external surface; and
attaching the second reaming member to the base with the second attachment mechanism.

According to a fourth aspect of the present invention, there is provided a method of surgery. The method may include the steps of:
providing a base comprising a connector adapted to couple the base to a driver and an external surface defining a support surface;
providing first reaming member having:
  a first internal surface shaped to seat the first reaming member on the support surface,
  a first external surface adapted to ream a bone to a first diameter, and
  a first attachment mechanism to attach the first reaming member to the base;
engaging the first internal surface with the support surface;
attaching the first reaming member to the base with the first attachment mechanism;
reaming a bone to the first diameter;
providing a second reaming member having:
  a second internal surface shaped to seat the second reaming member on the first external surface,
  a second external surface adapted to ream a bone to a second diameter larger than the first diameter, and
  a second attachment mechanism to attach the second reaming member to the base;
engaging the second internal surface with the first external surface;
attaching the second reaming member to the base with the second attachment; and
reaming the bone to the second diameter.

A BRIEF DESCRIPTION OF THE DRAWINGS

For a more complete understanding of the present invention and the advantages thereof, reference is now made to the following description taken in connection with the following drawings, in which.

DETAILED DESCRIPTION OF THE PREFERRED EMBODIMENTS

The present invention is a reamer. Part of the reamer is of a generally hemispherical shape fashioned to conform to the shape of, for example, a hip prosthesis. The exemplary reamer is intended to prepare and refine the interior surface of a pelvic socket known as an acetabulum for receipt of a cup part of a hip prosthesis.

The reamer includes a base to which reaming members are coupled. The reaming members include cutting features that are engageable with, for example, an acetabulum to remove and prepare the bone for receipt of a replacement cup.

The reamer includes a plurality of reaming members. A first reaming member of the plurality of reaming members has a first diameter. A second reaming member of the plurality of reaming members has a second diameter, larger than the first diameter. During a surgical procedure, the first reaming member is coupled to the base and used to ream the acetabulum to the first diameter. Afterwards, the second reaming member is coupled to the base and used to ream the acetabulum to the second, larger diameter.

The base of the reamer is a common base to which each one of the plurality of reaming members is couplable. The base provides a support structure to which reaming members are coupled. The support structure is a common structure providing support to the first and each successive reaming member.

In certain embodiments, a first reaming member with a first outer diameter is positioned over the base. A second reaming member with a second, larger outer diameter is positioned over the first reaming member and so on with the third, fourth, fifth, etc. reaming member. In this way, support is provided to each reaming member having incrementally increasing diameters by the nested stack of reaming members coupled to the base already.

In other embodiments, a first reaming member with a first outer diameter is coupled to the base and used for reaming. That first reaming member is removed from the base and a second reaming member with a second, larger outer diameter is coupled to the base. In this way, support is provided to each reaming member by the base.

Other alternative embodiments are of course possible, as a person of ordinary skill in the art would understand. However, it should be appreciated that the base is a common base capable of reaming connected to a reamer driver whilst reaming members with incrementally increasing diameters are coupled to it to thereby increase efficiency of a procedure in which a hemispherical cavity is prepared in a bone.

Figure 1:
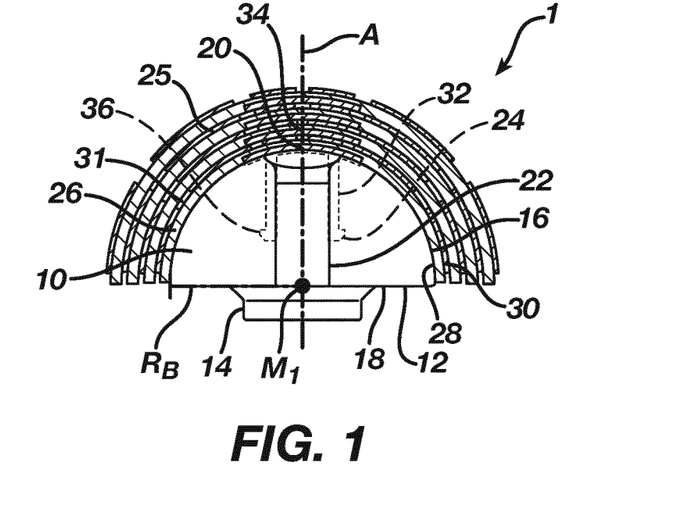
FIG. 1 shows a sectional side view of a reamer assembly of a first embodiment of the present invention.

A first embodiment of the present invention is shown by FIG. 1. The first embodiment is a reamer 1 for reaming a bone, such as an acetabulum. The reamer 1 has a base 10 and a plurality of reaming members 25. The plurality of reaming members 25 are couplable to the base 10 to form an assembly, which may be interchangeably referred to herein as a reamer 1 or a reaming assembly 1.

The base 10 has a connector surface 12 in which a connector 14 is defined. The connector 14 may be configured to receive a conventional reamer coupling, or it may be configured to receive a coupling 201 of a driver 200 shown in FIG. 15 or a coupling 301 of the driver 300 shown in FIG. 16. The driver 200 used to impart rotary motion to the reamer 1 in use.

The base 10 has a support surface 16. The support surface 16 has an external shape. The external shape is selected to provide a seating surface that supports the plurality of reaming members 25 in use.

The connector surface 12 is substantially planar. The connector surface 12 has a circular outer perimeter 18. The connector surface 12 has a midpoint $M_1$. The connector surface 12 has a radius $R_B$ measured as a straight line extending from the midpoint $M_1$ to the outer perimeter 18 of the connector surface 12.

With reference to FIG. 1, the support surface 16 is hemispherical in shape. Of course, this shape is merely exemplary and other support surface shapes are of course possible without departing from the scope of the invention.

The support surface 16 provides overall support and rigidity to each reaming member 25 arranged on the base. The support surface 16 is a hemispherical dome that extends from the outer perimeter 18 to a pole 20. The radius of the hemispherical dome is the same as the radius of the connector surface $R_B$. The radius $R_B$ is measured as a straight line extending from the midpoint $M_1$ to the outer edge of the support surface 16.

The pole 20 is located on an axis A. The axis A passes through the midpoint $M_1$ and extends perpendicular to the connector surface 12. A channel 22 extends parallel to the axis A through the support surface 16 from the pole 20 to the connector surface 12. The channel 22 has a groove 24 midway down.

Each reaming member 26 of the plurality of reaming members 25 has a seating surface 28, a reaming surface 30 and an attachment mechanism 32.

The seating surface 28 is the part of the reaming member 26 that is arranged over an underlying support surface.

The reaming surface 30 is the part of the reaming member 26 that is engaged with the acetabular for preparing the bone to receive an implant. The reaming surface 30 features cutter 31 arranged to remove bone and other tissue in preparation of the bone for receiving an implant.

The attachment mechanism 32 is the part of the reaming member 26 used to attach the reaming member 26 to the base 10.

The first reaming member 26 of the plurality of reaming members 25 to be connected to the base 10 is positioned on the support surface 16. Here, the seating surface 28 is positioned on the support surface 16.

The attachment mechanism 32 is a protrusion that extends from a pole 34 of the reaming member 26. The attachment mechanism 32 is arranged to be engaged with the channel 22. A hook 36 is defined at the end of the protrusion forming the attachment mechanism 32. The hook 36 engages the groove 24 to couple the reaming member to the base 10.

The channel 22 and the groove 24 in combination with the attachment mechanism 32 form a lock used to couple each reaming member 25 to the base 10.

Figure 2:
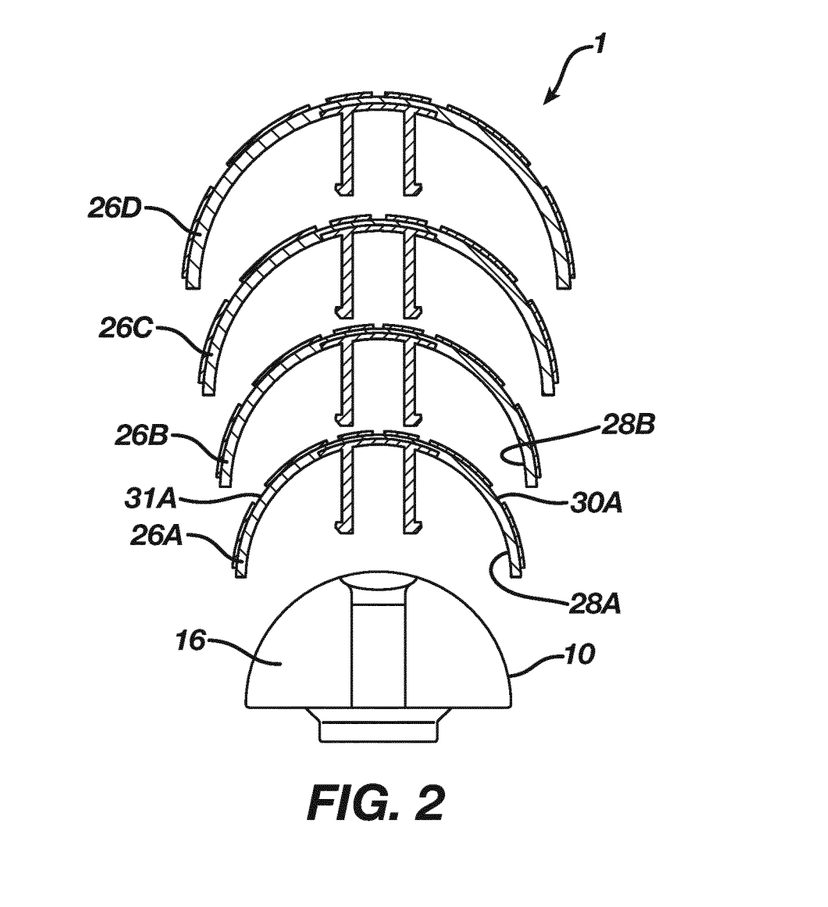
FIG. 2 shows an exploded sectional side of the reamer assembly shown in FIG. 1.

Referring to FIG. 2, each successive reaming member 26A, 26B, 26C, 26D is stacked on top of the reaming members already positioned on the base 10. For example, a first reaming member 26A is positioned on the base 10, a second reaming member 26B is positioned over the first reaming member 26A, and so on with the third and fourth reaming members 26C, 265D.

A portion of the first reaming member 26A is positioned on the support surface 16. The portion positioned on the base is a seating surface 28A of the first reaming member 26A. The reaming member subsequently positioned on the reaming assembly 1 is positioned over a reaming surface 30A covering the cutter 31A of the first reaming member 26A. In this way, the reaming surface 30A becomes a support surface over which a seating surface of the subsequent reaming member is seated.

In the first embodiment shown by FIG. 2, each successive reaming member 26A, 26B, 26C, 26D is positioned over the reaming member previously coupled to the reaming assembly 1. For example, a seating surface 28B of the second reaming member 26B is positioned on the reaming surface 30A of the first reaming member 26A. Each successive reaming member increases the diametric size of the reaming member 1 by a predetermined amount. The predetermined amount may be in the range of 0.5 to 2 mm. In a preferred embodiment, the predetermined amount is 1 mm. With this capability, the reaming assembly 1 may be used to efficiently ream a cavity of increasing diametric size without removal of the reaming assembly 1 from a driving instrument until a cavity of a desired size has been reamed by an operator.

FIG. 2 shows a reaming assembly 1 having four reaming members. As a person of skill in the art would understand, any number of reaming members may be positioned over the reaming members already positioned on and coupled to the base 10 to form the reaming assembly 1 used for reaming a cavity of a desired size.

In use, the first reaming member 26A is connected to the base 10 to form a reamer 1 having a first diameter. The reamer 1 is connected to a drive. The reamer 1 may be configured to be coupled to a conventional reamer coupling, or it may be configured to receive a coupling 201 of a driver 200 shown in FIG. 15 or a coupling 301 of the driver 300 shown in FIG. 16.

The reamer 1 is then engaged with the acetabular and driven to prepare the acetabulum to a first reaming diameter. The reamer 1 is removed and the acetabulum is visually assessed. If the acetabulum is to be reamed to a wider diameter, a second reaming member 26B is attached to the reamer 1. Since the reamer 1 is already connected to the driver 200, 300, the reamer 1 may be used to ream a cavity having a second, larger reaming diameter. This process is repeated to incrementally increase the reaming diameters until the physician or other operator has determined that the reamed cavity has a desired reaming diameter.

The base 10 is fabricated from a plastics material. Suitable plastics materials include polyacrylamide. For example, the base 10 may be made from a form of polyacrylamide marketed under the trade name IXEF. Of course, the base 10 may be fabricated from other suitable materials.

The base is made using plastic injection molding. Of course any other suitable manufacturing technique can be used to make the base 10.

Each reamer members 26A, 26B, 26C, 26D is fabricated from a metal material. Suitable metals include stainless steel. For example, Each reamer members 26A, 26B, 26C, 26D may be made from type 17-4 PH stainless steel. Of course, the base 10 may be fabricated from other suitable materials.

The reaming members 26A, 26B, 26C, 26D are manufactured using metal injection molding. Of course any other suitable manufacturing technique can be used to make the reamer members 26A, 26B, 26C, 26D.

Figure 3:
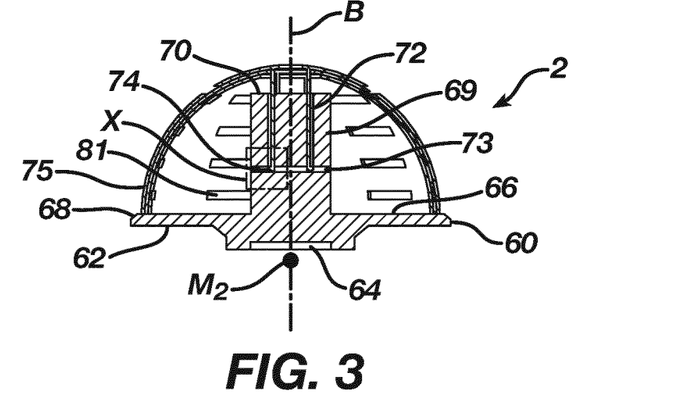
FIG. 3 shows a sectional side view of a reamer assembly of a second embodiment of the present invention.

FIG. 3 shows a reaming assembly 2 of a second embodiment of the present invention. The reaming assembly 2 has a base 60 and a plurality of reaming members 75. The plurality of reaming members 75 are couplable to the base 60 to form the reaming assembly 2. Similarly to the first embodiment, the reaming members 75 are stacked on top of each to form reamer assemblies having increasing diametrical size.

The base 60 has a connector surface 62 in which a connector 64 is defined. The connector 64 is configured to receive a coupling 201 of a driver. The driver may be a conventional driver, a driver 200 shown in FIG. 15, or the reamer 300 shown in FIG. 16, or any other suitable driver. The driver is used to impart rotary motion to the reamer 2 in use.

The base 60 has a support surface 66. The support surface 66 has a substantially planar surface.

The base 60 has an outer perimeter 68 defining a circularly-shaped edge of the base 60. The connector surface 62 and the support surface 66 as spaced apart by the outer perimeter 68.

A column 69 is located on the support surface 66. The column 69 is a shaft that extends from its base on the support surface 66 to an apex 70. The column 69 is located on an axis B that passes through a midpoint $M_2$ and extends perpendicularly from the connector surface 66.

A channel 72 extends parallel to the axis B from the apex 70 towards the support surface 66.

A passage 73 is located in a central region of the column 69. The passage 73 intersects with the channel 72. An opening 74 is formed where the passage 73 intersects with the channel 72.

Figure 4:
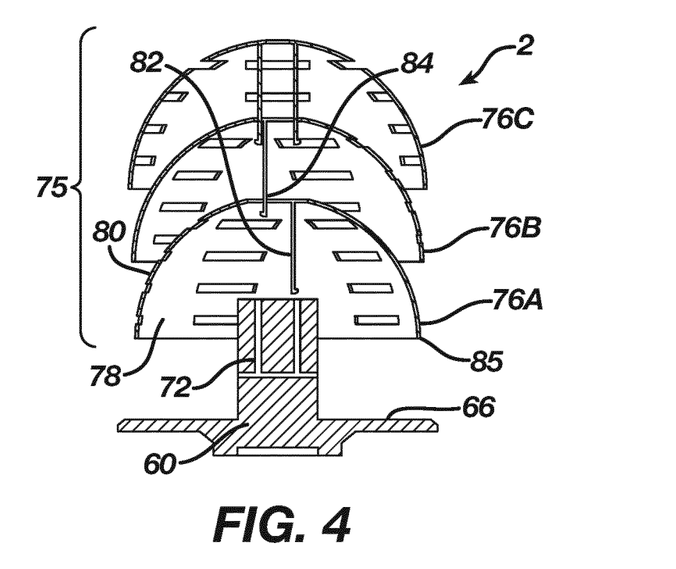
FIG. 4 shows an exploded sectional side view of the reamer assembly shown in FIG. 3.

Referring to FIG. 4, each reaming member 76A, 76B, 76C of the plurality of reaming members 75 has an internal surface 78, an external, reaming surface 80 and an attachment mechanism 82. The reaming surface features a plurality of cutters 81 arranged for preparation of the bone to receive an implant.

Each reaming member 76A, 76B, 76C has a hemispherical shape with a pole 84 that extends to an equator 85.

The internal surface 78 is the part of the reaming member 76A, 76B, 76C that faces towards the support surface 66, when the reaming member 76A, 76B, 76C is arranged on the reaming assembly 2.

The reaming surface 30 is the part of the reaming member 76A, 76B, 76C that is engaged with the acetabular for preparing the bone to receive an implant.

The attachment mechanism 82 is the part of the reaming member 76A, 76B, 76C used to attach the reaming member 76A, 76B, 76C to the base 60. The attachment mechanism 82 is a protrusion that extends from a pole 84 of the reaming member 76A, 76B, 76C. The attachment mechanism 82 is resilient.

The attachment mechanism 82 is configured to engage the channel 72 to couple the reaming member 76A, 76B, 76C to the base 60.

The channel 72 and the opening 74 in combination with the attachment mechanism 82 form a lock used to couple each reaming member 25 to the base 10. The lock is latch-like.

Figure 5:
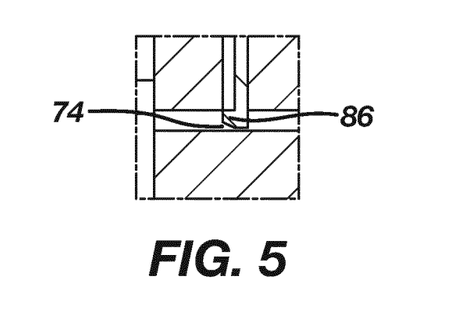
FIG. 5 shows an expanded view of a portion X shown of FIG. 3 showing a connection feature used to couple a reaming member to a base of the reamer assembly shown in FIG. 3.

Referring to FIG. 5, a hook 86 is defined at the end of the protrusion forming the attachment mechanism 82. The hook 86 is capable of engaging the opening 74 to couple the reaming member to the base 10.

The attachment mechanism 82 is sprung biased towards a position that enables the hook 86 to engage the opening 74. Engagement of the hook 86 with the opening 74 couples the reaming member 76A, 76B, 76C to the base 60.

Figure 6:
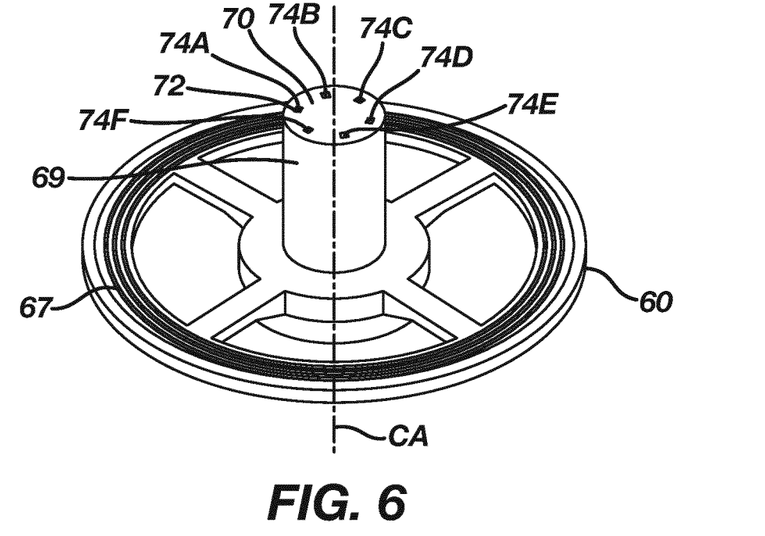
FIG. 6 shows a perspective view of a base of the reamer assembly shown in FIG. 3.

With reference to FIG. 6, the column 69 includes a plurality of channels 72. The plurality of channels 72 extend from the apex 70 into the column 69. The column includes six channels 72 each with an opening 74A, 74B, 74C, 74D, 74E, 74F on the surface forming the apex 70. Each opening 74A, 74B, 74C, 74D, 74E, 74F and corresponding channel 72 is square in shape.

The openings 74A, 74B, 74C, 74D, 74E, 74F are spaced apart about the apex 70. The openings 74A, 74B, 74C, 74D, 74E, 74F are equidistant from each other.

The column 69 has a central axis CA. Each opening 74A, 74B, 74C, 74D, 74E, 74F and corresponding channel 72 is equidistant from each other and from the central axis CA.

Openings 74A, 74B, 74C, 74D, 74E, 74F and their corresponding channel 72 form pairs. The pairs are formed by openings on sides of the column 69 that are radially opposed from each other relative to the central axis CA. A first pair is formed by openings 74A, 74D. A second pair is formed by openings 74B, 74E. A third pair is formed by openings 74C, 74F.

Each pair is arranged to receive and retain an attachment mechanism 82 of a reaming member 75 of the plurality of reamer members 76A, 76B, 76C.

The base 60 includes a plurality of grooves 67. Each groove 67 is arranged to receive the reaming member 75 and to minimize deformation of the reaming member 75 during a reaming procedure.

Figure 7:
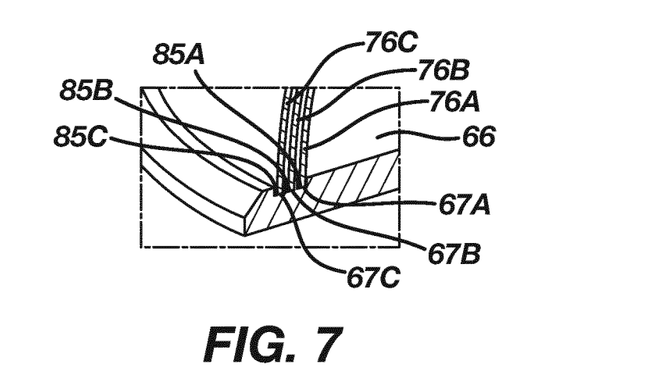
FIG. 7 shows a perspective view of a portion of the reamer assembly shown in FIG. 3.

Referring to FIG. 7, the support surface 66 includes the plurality of grooves 67A, 67B, 67C. Each groove 67A, 67B, 67C is circular in shape. Each groove 67A, 67B, 67C is arranged to receive an equator 85A, 85B, 85C, respectively, of the remaining members 76A, 76B, 76C. Each groove 67A, 67B, 67C has a width selected to receive its respective equator 85A, 85B, 85C. The width is chosen so that the equator snuggly fits into the groove.

Each groove 67A, 67B, 67C has a diameter. Each groove 67A, 67B, 67C has a diameter selected to receive the equator 85A, 85B, 85C of its respective reaming member 76A, 76B, 76C.

The first reaming member 76A is the first of the plurality of reaming members 75 to be connected to the base 10. The first reaming member 76A has the smallest diameter when compared to the second and third reaming members 76B, 76C. The second reaming member 76B has a diameter larger than the first reaming member 76A and smaller than the third reaming member 76C. The third reaming member 76C has the largest diameter.

The diameters of the reaming assembly increase as each successive reaming member 76A, 76B, 76C is located on the underlying reamer members. The final diameter, for example of the largest reaming member, is corresponds to the overall diameter of a cavity to be prepared in a bone. For example, the final diameter could be 36 mm. The diameters of the reaming members may increase increments of 2 mm until the final diameter is reached. For example, the reaming member 76A could have a diameter of 32 mm, the remain member 76B could have a diameter of 34 mm and the reaming member 76C could have a diameter of 36 mm. In another example, the final diameter could be 62 mm. in this example, the reaming member 76A could have a diameter of 58 mm, the remain member 76B could have a diameter of 60 mm and the reaming member 76C could have a diameter of 62 mm. The final reaming diameters and the increments can of course vary, as a person of ordinary skill would understand. The diameters of grooves and equators are varied to correspond to the diameters of the reaming members 76A, 76B, 76C as a person of ordinary skill would understand.

Whilst the second embodiment has been described as having three remaining members, a person of skill in the art would of course understand that any number of reaming members are of course possible within the scope of the present invention.

Referring to FIG. 4, in a first configuration, the first reaming member 76A is coupled to the base 60 and used to ream a cavity in a bone of a first dimension. In a second configuration, the second reaming member 76B is coupled to the base 60 and used to ream a cavity in a bone of a second dimension.

Figure 8:
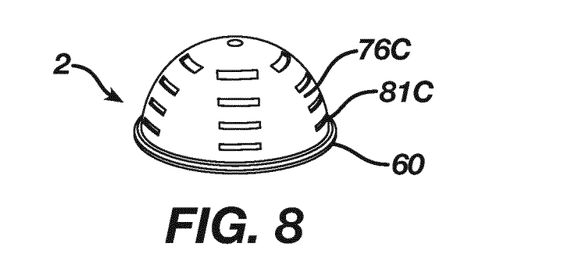
FIG. 8 shows a perspective view of the reamer assembly shown in FIG. 3.

In a third configuration, with reference to FIG. 8, the third reaming member 76C is coupled to the base 60 to form a reaming assembly 2 having a third diameter. In the third configuration, the reaming assembly 2 is used to ream a cavity having a third dimension using the plurality of cutters 81C.

The materials used for the second embodiment correspond with the materials used for the first embodiment.

Figure 9:
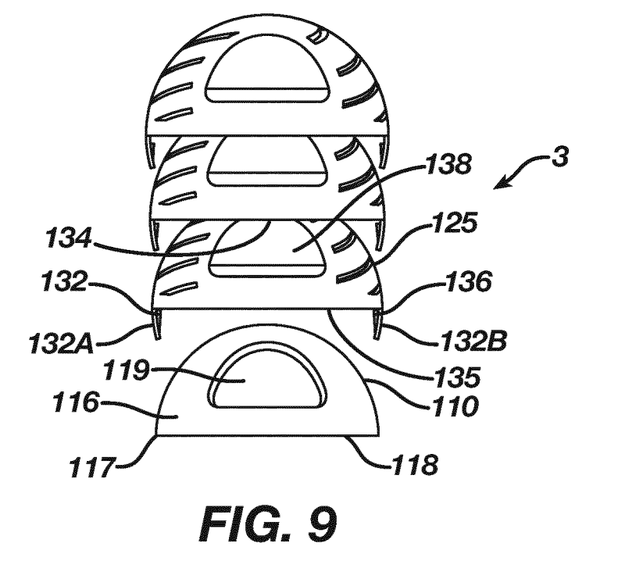
FIG. 9 shows an exploded front view of a reaming assembly of a third embodiment of the present invention.

FIG. 9 shows a reaming assembly 3 of a third embodiment of the present invention. The reaming assembly 3 has a base 110 and a plurality of reaming members 125. The plurality of reaming members 125 are couplable to the base 110 to form a reaming assembly 3. Similarly to the first and second embodiments, the reaming members 125 are stacked on top of each to form reamer assemblies having increasing diametrical sizes.

The reaming assembly 3 is substantially the same as the reaming assembly of the first embodiment with the exception of the attachment mechanism.

In the third embodiment, the reaming assembly 3 has a base 110 to which an attachment mechanism 132 of a reaming member 125 is coupled.

The base 110 has an edge 117 defined where its substantially hemispherical support surface 116 meets its substantially planar connector surface 112.

The base 110 has a first and second opening 119 located on either side of the support surface 116. The opening 119 is substantially semi-circular in shape.

The reaming member 125 has a pole 134 that extends to an equator 135. The equator 135 defines the perimetrical base of the reaming member 125. The attachment mechanism 132 has a first and second protrusion 132A, 132B extending from the equator 135. Each protrusion 132A, 132B is resilient. Each protrusion 132A, 132B features a hook 136. The hook 136 is arranged to engage the edge 117 to couple the reaming member 125 to the base 110.

The edge 117 in combination with the attachment mechanism 132 form a lock used to couple reaming members 125 to the base 110.

The third embodiment also has features to minimize rotation of the reaming member 125 relative to the base 110. The channel 119 of the base and a first and second indent 138 arranged on either side of the reaming member 125 provide the anti-rotation features.

Figure 10A:
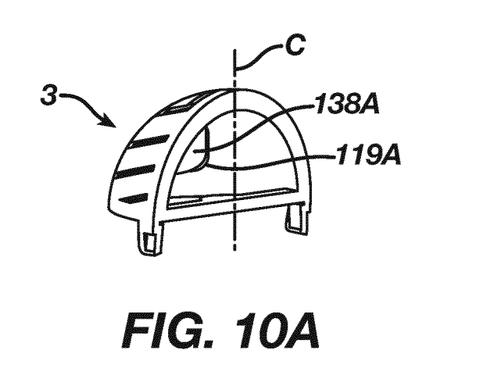
FIG. 10A shows a sectional view of one side of the reaming assembly of FIG. 8.
Figure 10B:
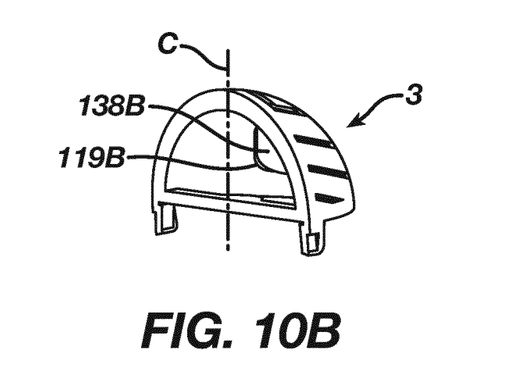
FIG. 10B shows a section view of the other side of the reaming assembly shown in FIG. 9A.

With reference to FIGS. 10A and 10B, the reaming assembly 3 is assembled. FIG. 10A shows a first side of the reaming assembly 3 in which a first indent 138A is arranged the first opening 119A. FIG. 10B shows an opposed second side of the reaming assembly 3 in which a second indent 138B is arranged a second opening 119B. In operation, with the indents 138A, 138B located through the openings 119A, 119B, rotation of the reamer assembly 3 about the axis C causes the indents 138A, 138B to abut the sidewall defining the openings 119A, 119B to minimize rotation of the reaming member or reaming members 125 coupled to the base 110.

Figure 11:
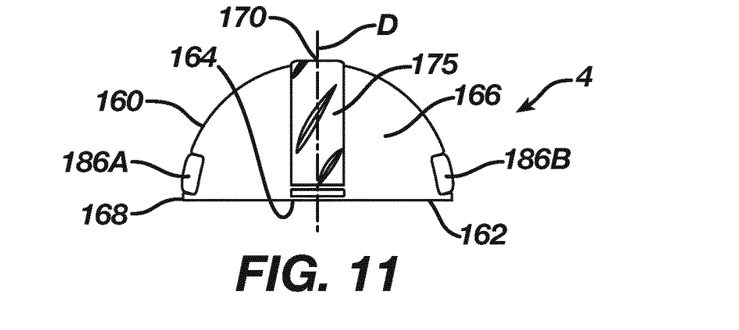
FIG. 11 shows a side view of a reaming assembly of a fourth embodiment of the present invention.

A fourth embodiment of the present invention is shown by FIG. 11. The fourth embodiment is a reamer assembly 4 for reaming a bone, such as an acetabulum. The reamer assembly 4 has a base 160 and a plurality of reaming members 175. The plurality of reaming members 175 are couplable to the base 160 to form an assembly, which may be interchangeably referred to herein as a reamer 4 or a reaming assembly 4.

The base 160 has a connector surface 162 in which a connector 164 is located. The connector 164 may be configured to receive a driver coupling. The driver coupling may be a coupling of a conventional reamer coupling, or it may be a coupling 201 of a driver 200 shown in FIG. 15 or a coupling 301 of the driver 300 shown in FIG. 16, or any other suitable driver coupling. The driver 200, 300 is used to impart rotary motion to the reamer 1 in use.

The base 160 has a support surface 166. The support surface 166 has an external shape. The external shape is selected to provide a seating surface that supports the plurality of reaming members 175 in use.

The support surface 166 extends from an outer perimeter 168 to a pole 170. The pole 170 is located on an axis D about which the reaming assembly 4 is rotated by the reamer driver 200, 300.

The support surface 166 provides overall support and rigidity to each reaming member 175 arranged on the base. The support surface 166 is a hemispherical dome. Of course, this shape is merely exemplary and other support surface shapes are of course possible without departing from the scope of the invention.

Figure 12:
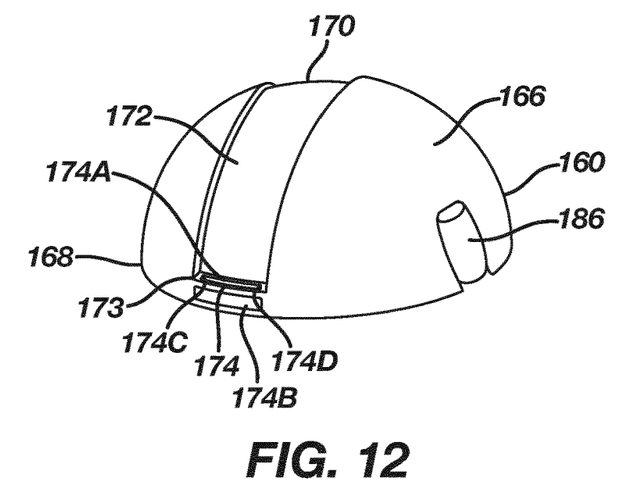
FIG. 12 shows a perspective view of a base of the reaming assembly shown in FIG. 11.

With reference to FIG. 12, the support surface 166 has a groove 172. The groove 172 extends longitudinally from the pole 170 to the outer perimeter 168. In the preferred embodiment, the pole 170 is the midpoint of the groove 172. The groove 172 extends away from the pole 170 in both longitudinal directions towards opposed sides of the outer perimeter 168.

The groove 172 ends adjacent the outer perimeter at a step 173. The step 173 features a reamer member coupling 174. The reamer member coupling 174 has a slot 174A and a button 174B.

The slot 174A is arranged to receive a portion of the reaming member 175 to couple the reaming member 175 to the body 160. A first and second tooth 174C, 174D are arranged on latitudinally opposed sides of the slot 174A.

The button 174B is capable of being depressed to release the reaming members 175 from the slot 174A.

The groove 172 is dimensioned to receive the reaming members 175 with a tight fit. The tight fit minimizes rotation of the remaining members 175 relative to the base 160.

The groove 172 has a width of approximately 20% of diameter of the selected reaming member 175. For example, where a reaming assembly 4 has a diameter of 36 mm, the groove has a width of 7.2 mm. For example, where a reaming assembly 4 has a diameter of 63 mm the groove has a width of 12.3 mm.

The groove has a depth of 1.2 mm. These dimensions are selected to provide the tight fit with the reaming members 175.

The base 160 features a set of alignment rollers 186.

With reference to FIG. 11, the set of alignment rollers 186 includes a first and a second alignment roller 186A, 186B. The alignment rollers are located on opposed sides of the base 160. In use, the set of alignment rollers 186 serve the purpose of aligning the reamer head assembly 4 with the cavity being reamed.

With reference to FIG. 11, the reaming member 175 is engageable with the base 160 to form a reaming assembly 4.

Figure 13:
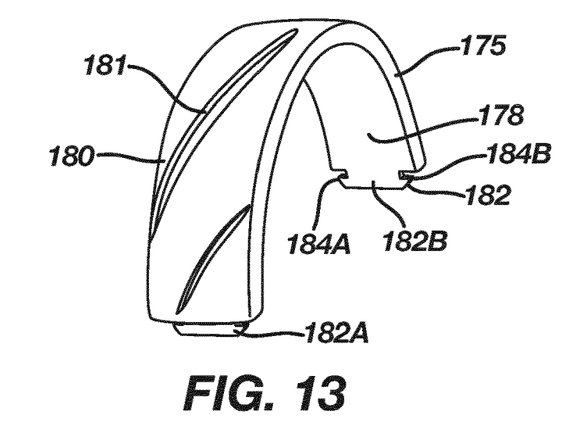
FIG. 13 shows a perspective view of a reaming member of the reaming assembly shown in FIG. 11.

FIG. 13 shows the reaming member 175. The reaming member 175 resembles a curved band. The reaming member 175 is shaped to match the shape of the groove 172. The reaming member 175 has a width that corresponds to the width of the groove 172 as described above. The shape and width are chosen to enable a tight fit to be formed between the reaming member 175 and the groove 172.

The reaming member 175 has a seating surface 178, a reaming surface 180 and an attachment mechanism 182.

The seating surface 178 is configured to be arranged over the underlying support surface 166.

The reaming surface 180 is the part of the reaming member 175 that is engaged with the acetabular for preparing the bone to receive an implant. The reaming surface 180 features cutters 181 arranged to remove bone and other tissue in preparation of the bone for receiving an implant.

The seating surface 178, reaming surface 180 and attachment mechanism 182 of the reaming member 175 form the body of the reaming member in which the cutters 181 are arranged.

The reamer member coupling 174 and attachment mechanism 182 form a lock used to attach the reaming member 175 to the base 160.

The attachment mechanism 182 has a first and second protrusion 182A, 182B. The first and second protrusion extend from opposed ends of the reaming member 175.

Each protrusion 182A, 182B has a first and a second hook 184A, 184B.

Figure 14:
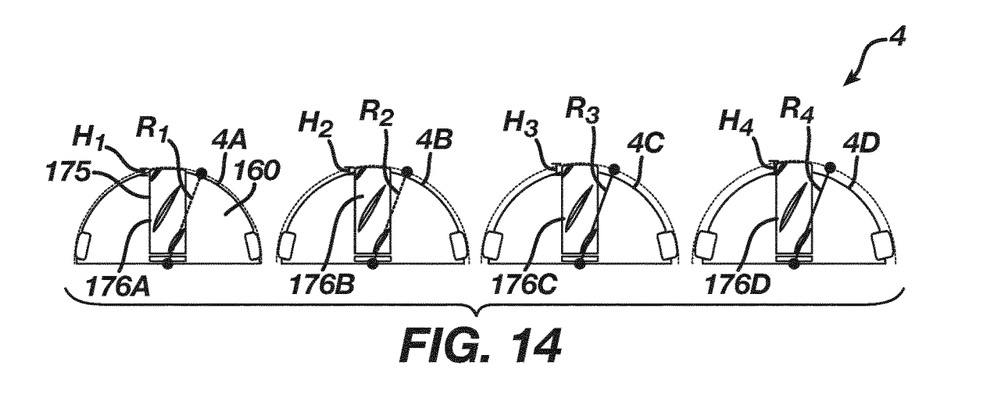
FIG. 14 shows a series of front views of differently sized reaming members positioned on the base of the reaming assembly shown in FIG. 10.

FIG. 14 shows a plurality of reaming assembles 4. The plurality of reaming assemblies 4 have a common base 160 upon which a reaming member 175 of a plurality of reaming members 176A, 176B, 176C, 176D is arranged.

The plurality of reaming members 176A, 176B, 176C, 176D have differing heights $H_1$, $H_2$, $H_3$, $H_4$.

The first reaming member 176A has a height $H_1$.
The second reaming member 176B has a height $H_2$.
The third reaming member 176C has a height $H_3$.
The fourth reaming member 176D has a height $H_4$.

The heights $H_1$, $H_2$, $H_3$, $H_4$ increase successively. For example, the height $H_1$ is smaller than the height $H_2$, the height $H_2$ is smaller than the height $H_3$, and the height $H_3$ is smaller than the height $H_4$.

The heights may increase in 0.5 mm increments. In one example, the reaming assembly 4, could be used to ream a cavity with a final diameter of 32 mm. The reaming members could increase in 0.5 mm increments starting from 30 mm. In another example, the final diameter could be 62 mm. In this example, the reaming members could start at a reaming diameter of 60 mm. The final reaming diameters and the increments can of course vary, as a person of ordinary skill would understand.

The variability of the heights $H_1$, $H_2$, $H_3$, $H_4$ enables an operator to successively increase the radius of the reaming assembly 4. The successive increase in radius enables staged preparation of a cavity in a bone by an operator. For example, in a first stage, a first reamer combination 4A having the first reaming member 176A arranged on the common base 160 defines a reaming assembly 4 having a first radius $R_1$. The operator can use this first reamer combination 4A to ream a cavity with a first diameter D1. In a second stage, a second reamer combination 4B having the second reaming member 176B arranged on the common base 160 defines a reamer assembly 4 having a second radius $R_2$. The operator can use this second reamer combination 4B to ream a cavity with a second diameter, which is larger than the first diameter. This process of successively increasing the radius of the reamer assembly 4 in stages is repeated with a third reamer combination 4C, a fourth reamer combination 4D and so on with other reamer combinations of increasing radii until the operator has prepared a cavity in a bone of the desired diameter.

For ease of reference, the radii $R_1$, $R_2$, $R_3$, $R_4$ have been depicted by the imaginary dotted lines shown in FIG. 14.

To form the combinations 4A, 4B, 4C, 4D, respective reaming members 176A, 176B, 176C, 176D are coupled to the base 160 by engaging the respective attachment mechanism 182 with the reamer member coupling 174.

Figure 15:
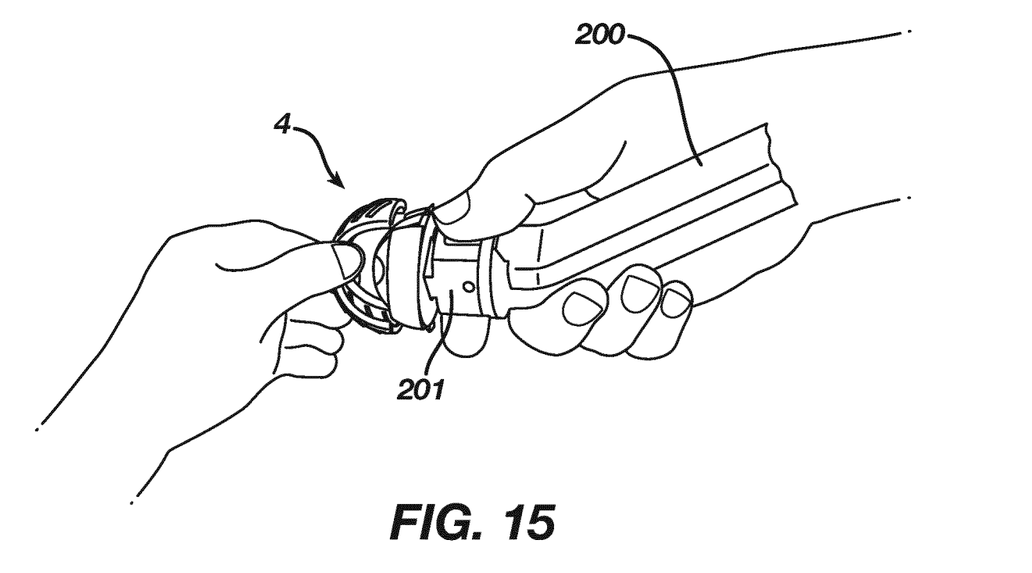
FIG. 15 shows an exemplary reamer driver arranged to be coupled to a reaming assembly of FIG. 10.
Figure 16:
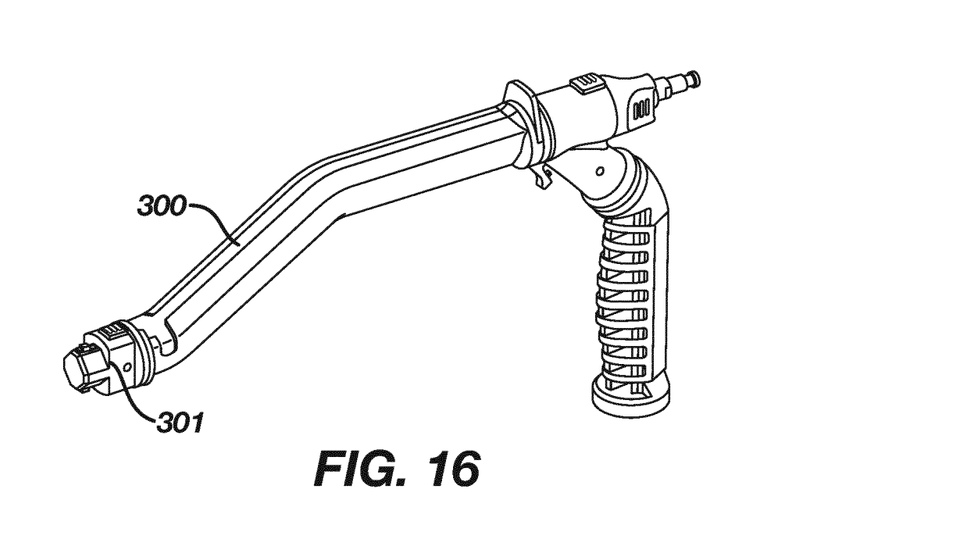
FIG. 16 shows another exemplary reamer driver.

With reference to FIG. 15, a reamer 4 is configured for use by connecting it to a reamer driver. The reamer 4 is coupled to the driver to be used in a reaming process. During the reaming process, the reamer 4 is engaged with a portion of a bone that is to be reamed. The reamer driver, to which the reamer 4 is coupled, is activated to rotate the reamer 4. The rotating reamer 4 is pressed against a bone to form a cavity.

In a first stage, the base 160 of the reamer 4 is coupled to coupling 201 of an exemplary reamer 200.

An operator, with knowledge of a final radius of a cavity to be formed in a bone, selects a reaming member 175 having a radius of smaller than the final radius. For example, the operator may select a reaming member 176A.

The operator then couples the reaming member 175 to the base 160 to form a first, starter, reamer 4.

The reamer 4 having a radius of smaller than the final radius is engaged with a portion of a bone that is to be reamed. The reamer driver 200 is activated to rotate the reamer 4. The rotating reamer 4 is pressed against a bone to form a starter cavity. The starter cavity has a radius of smaller than the final radius.

After the start cavity has been formed, an operator removes the in situ reaming member 175. The operator then selects a reaming member with an increased radius and couples it to the base 160.

The operator repeats this process until a cavity of a desired depth and radius is formed in the bone.

The reaming members 176A, 176B, 176C, 176D are coupled to the base 160 using the first and second protrusions 182A, 182B. The protrusions 182A, 182B are pushed into the slots 174A located on either side of the base 160. The reaming member 176A, 176B, 176C, 176D is pushed or pressed until its hooks 184A, 184B are engaged by the teeth 174C, 174D. With the teeth 174C, 174D engaged with the hooks 184A, 184B, one of the combinations 4A, 4B, 4C, 4D is formed and can be used by an operator for reaming purposes described above.

After reaming has been performed, and an operator intends to ream a cavity having a larger diameter, the buttons 174B on either side of the base 160 can be depressed to enable removal of the reaming member 176A, 176B, 176C, 176D that is presently attached to the base 160. Depressing the buttons 174B releases the hooks 184A, 184B from the respective tooth 174C, 174D so that the reaming member 176A, 176B, 176C, 176D may be removed from the base by an operator.

In the exemplary embodiment shown by FIGS. 11-14, the base 160 is fabricated from a plastics material. Suitable plastics materials include polyacrylamide. For example, the base 160 may be made from a form of polyacrylamide marketed under the trade name IXEF. Of course, the base 160 may be fabricated from other suitable materials.

The body 178, 180, 182 of the reaming member 175 is fabricated from a plastics material. Suitable plastics materials include polyacrylamide. For example, the reaming member 175 may be made from a form of polyacrylamide marketed under the trade name IXEF. Of course, the reaming member 175 may be fabricated from other suitable materials.

The cutters 181 are fabricated from a metal material. Suitable metals include stainless steel. For example, Each reamer members 26A, 26B, 26C, 26D may be made from type 17-4 PH stainless steel. Of course, the cutters 181 may be fabricated from other suitable materials.

The base 160 and the body 178, 180, 182 of the reaming member 175 are manufactured using plastic injection molding. The cutters 181 are fabricated by punching the cutter out of a metal sheet, sharpening an edge to form a blade. The cutter 181 is then arranged and secured to a desired location in the body 178, 180, 182 of the reaming member 175.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

Although preferred embodiments of the present invention have been shown and described, it will be appreciated by those skilled in the art that changes may be made without departing from the scope of the invention as defined in the claims.

In this specification, the terms "comprise", "comprises", "comprising" or similar terms are intended to mean a non-exclusive inclusion, such that a system, method or apparatus that comprises a list of elements does not include those elements solely, but may well include other elements not listed.

The reference to any prior art in this specification is not, and should not be taken as, an acknowledgement or any form of suggestion that the prior art forms part of the common general knowledge.

It will of course be understood that this description is by way of example only; alterations and modifications may be made to the described embodiment without departing from the scope of the invention as defined in the claims.

The invention claimed is:

1. A system for reaming a bone comprising:
a base comprising (i) a connector at a proximal end of the base adapted to couple the base to a driver and (ii) a support surface at a distal end of the base;
a first reaming member comprising (i) a first seating surface shaped to seat the first reaming member over the support surface, (ii) a first reaming surface adapted to ream a bone to a first diameter, and (iii) a first attachment mechanism attaching the first reaming member to the base;
a second reaming member comprising (i) a second seating surface shaped to seat the second reaming member over the first reaming surface;
(ii) a second reaming surface adapted to ream a bone to a second diameter, and (iii) a second attachment mechanism attaching the second reaming member to the base;
wherein (i) the second diameter is larger than the first diameter, and (ii) the first reaming surface provides a support surface to the second reaming member such that the first reaming member is nested within the second reaming member.

2. The assembly of claim 1, wherein the first and second reaming members are releasably attachable to the base.

3. The assembly of claim 2, wherein the second reaming surface is separated from the first reaming surface by a predetermined thickness to thereby increase the second diameter relative to the first diameter.

4. The assembly of claim 3, wherein the support surface of the base has an external shape and the first seating surface has an internal shape that matches the external shape.

5. The assembly of claim 4, wherein the external shape is hemispherical and the internal surface has a curvature that conforms to the external shape.

6. The assembly of claim 5, wherein the base comprises a first recess extending into the support surface, the first reaming member comprises a first prong and a second recess extending into the support surface provided in the first reaming surface, and the second reaming member comprises a second prong;
wherein the first recess is configured to receive the first prong in order to attach the first reaming member to the base; and
wherein the second recess is configured to receive the second prong in order to attach the second reaming member to the base.

7. The assembly of claim 5, wherein the second reaming member positioned over the first reaming member is attached to the first reaming member by the second attachment mechanism in order to attach the second reaming member to the base.

8. A kit comprising:
a base comprising (i) a connector at a proximal end of the base adapted to couple the base to a driver and (ii) a support surface at a distal end of the base;
a first reaming member comprising (i) a first seating surface shaped to seat the first reaming member over the support surface, (ii) a first reaming surface adapted to ream a bone to a first diameter, and (iii) a first attachment mechanism configurable to attach the first reaming member to the base; and
a second reaming member comprising (i) a second seating surface shaped to seat the second reaming member over the the first reaming surface;
(ii) a second reaming surface adapted to ream a bone to a second diameter, and iii) a second attachment mechanism configurable to attach the second reaming member to the base;
wherein (i) the second diameter is larger than the first diameter, and (ii) the first reaming surface provides a support surface to the second reaming member such that the first reaming member is nested within the second reaming member when the first reaming member and second reaming member are attached to the base.

* * * * *